(12) United States Patent
Yazawa et al.

(10) Patent No.: US 9,086,393 B2
(45) Date of Patent: Jul. 21, 2015

(54) SENSOR CONTROL DEVICE AND SENSOR CONTROL METHOD

(75) Inventors: Katsunori Yazawa, Komaki (JP); Yuji Kimoto, Komaki (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 659 days.

(21) Appl. No.: 13/501,205

(22) PCT Filed: Oct. 6, 2010

(86) PCT No.: PCT/JP2010/005993
§ 371 (c)(1),
(2), (4) Date: Apr. 10, 2012

(87) PCT Pub. No.: WO2011/045908
PCT Pub. Date: Apr. 21, 2011

(65) Prior Publication Data
US 2012/0210174 A1    Aug. 16, 2012

(30) Foreign Application Priority Data

Oct. 13, 2009  (JP) ................................. 2009-236017

(51) Int. Cl.
| | |
|---|---|
| *G06F 11/14* | (2006.01) |
| *G01N 33/00* | (2006.01) |
| *G01N 27/419* | (2006.01) |
| *G01R 31/28* | (2006.01) |

(52) U.S. Cl.
CPC .......... *G01N 33/0037* (2013.01); *G01N 27/419* (2013.01); *G01N 33/007* (2013.01); *G01R 31/2829* (2013.01)

(58) Field of Classification Search
CPC ......... G06F 11/30; G06F 17/00; G01N 27/41; G01N 27/407; G01N 33/0016; G01N 27/4074; G01N 27/419; G01N 27/02
USPC .................. 702/183, 185; 73/23.32; 204/406; 375/76
See application file for complete search history.

(56) References Cited

U.S. PATENT DOCUMENTS

| | | | | |
|---|---|---|---|---|
| 4,915,813 | A * | 4/1990 | Nakajima et al. ............. | 204/406 |
| 5,001,726 | A * | 3/1991 | Kawai et al. .................. | 375/317 |
| 5,980,710 | A * | 11/1999 | Kurokawa et al. ............ | 204/425 |
| 6,099,717 | A * | 8/2000 | Yamada et al. ............ | 205/784.5 |
| 6,478,940 | B1 * | 11/2002 | Suzuki et al. ................. | 204/425 |

(Continued)

FOREIGN PATENT DOCUMENTS

| | | |
|---|---|---|
| JP | 7-59221 A | 3/1995 |
| JP | 2004-205488 A | 7/2004 |

*Primary Examiner* — John Breene
*Assistant Examiner* — Mohammad K Islam
(74) *Attorney, Agent, or Firm* — Sughrue Mion, PLLC (57) ABSTRACT

A sensor control device including an anomaly diagnosis section. When at least one of a first $NO_X$ concentration Ip2W based on the output OP1 of a first differential amplification circuit (210) and a second $NO_X$ concentration Ip2N based on the output OP2 of a second differential amplification circuit (220) falls within an anomaly diagnosis range ZN, the difference D between Ip2W and Ip2N is obtained, and the difference D is stored in a difference accumulation buffer BF such that 16 values of the difference D continuously sampled up to the present are stored. The integrated value (difference integral value) Dint of the difference D is obtained. When the difference integrated value Dint becomes equal to or greater than a predetermined value Di0, the sensor control device indicates a diagnosis result of "anomalous."

9 Claims, 7 Drawing Sheets

(56) References Cited

U.S. PATENT DOCUMENTS

| | | | |
|---|---|---|---|
| 7,416,649 B2 * | 8/2008 | Ieda et al. | 204/401 |
| 7,481,913 B2 * | 1/2009 | Kawase et al. | 204/406 |
| 7,802,463 B2 * | 9/2010 | Inoue et al. | 73/23.32 |
| 2004/0089545 A1 | 5/2004 | Kawase et al. | |

* cited by examiner

SENSOR CONTROL DEVICE AND SENSOR CONTROL METHOD

CROSS REFERENCE TO RELATED APPLICATIONS

This application is a National Stage of International Application No. PCT/JP2010/005993 filed Oct. 6, 2010, and which claims benefit to Japanese Patent Application No. 2009-236017 filed Oct. 13, 2009, the contents of which are incorporated herein by reference in their entirety.

TECHNICAL FIELD

The present invention relates to a sensor control device and a sensor control method for controlling a sensor.

BACKGROUND ART

Conventionally, there has been known a sensor for detecting the concentration of nitrogen oxides (hereinafter, simply referred to as "$NO_X$"), which is a specific type of gas contained in exhaust gas of an internal combustion engine. A proposed sensor control device which is connected to such a sensor is configured to amplify the output of the sensor by two amplification circuits operating in a wide range and a narrow range, respectively; selects one of the two amplified signals; and obtain the $NO_X$ concentration on the basis of the selected signal (see Patent Document 1). This proposed sensor control device can improve the detection accuracy of $NO_X$ concentration.

PRIOR ART DOCUMENT

Patent Document

Patent Document 1: Japanese Patent Application Laid-Open (kokai) No. 2004-205488

Although the above-described sensor control device can diagnose or detect a failure in which one of input signals fed from the two amplification circuits to a control section (e.g., a microcomputer) becomes anomalous because of GND short (short to the ground) or short to a drive voltage (power supply voltage), the above-described sensor control device has a problem in that it cannot diagnose or detect a failure in which an input signal(s) assumes an anomalous value in an intermediate range between the GND and the drive voltage. The failure in which an input signal(s) assumes an anomalous value in the intermediate range occurs, for example, due to deterioration of the corresponding amplification circuit with time or erroneous mounting of parts of the corresponding amplification circuit. When such a failure occurs, the corresponding input signal assumes a fixed value in the intermediate range, or the gain or offset of the amplification circuit becomes improper, and the input signal assumes a value different from the desired value.

SUMMARY OF THE INVENTION

Problems to be Solved by the Invention

An object of the present invention is to perform accurate diagnosis of a failure in which an input signal from an amplification circuit assumes an anomalous value in an intermediate range between the GND and a drive voltage (hereinafter, the intermediate range between GND and Vcc will be simply referred to as the "intermediate range").

Means for Solving the Problems

The present invention has been conceived for solving, at least partially, the above problem and can be embodied in the following modes or Application examples.

Application Example 1

A sensor control device comprising a sensor section which outputs an electric signal value corresponding to a physical or chemical characteristic of a measurement subject; a first amplification section which receives the electric signal value output from the sensor section and amplifies the electric signal value at a first amplification factor for a first detection range of the characteristic; a second amplification section which receives the electric signal value output from the sensor section and amplifies the electric signal value at a second amplification factor for a second detection range of the characteristic, at least a portion of the second detection range overlapping with the first detection range; and a control section which obtains a value representing the characteristic on the basis of an output from the first amplification section and an output from the second amplification section, and which outputs the value as a sensor detection value. The sensor control device is characterized by further comprising an equivalent value acquisition section for acquiring a first characteristic equivalent value based on the output from the first amplification section and a second characteristic equivalent value based on the output from the second amplification section; an equivalent value determination section for determining whether or not at least one of the first and second characteristic equivalent values falls within an anomaly diagnosis range, which is a predetermined range contained in an overlap portion between the first detection range and the second detection range; and an anomaly diagnosis section configured such that, when the equivalent value determination section determines that at least one of the first and second characteristic equivalent values falls within an anomaly diagnosis range, the anomaly diagnosis section determines whether or not an anomaly has occurred in at least one of a signal system containing the first amplification section and a signal system containing the second amplification section, through comparison between the first characteristic equivalent value and the second characteristic equivalent value.

Application Example 2

A sensor control device according to Application example 1, wherein the anomaly diagnosis section comprises a difference calculation section for calculating the difference between the first characteristic equivalent value and the second characteristic equivalent value; and an anomaly determination section for determining the occurrence of an anomaly on the basis of the calculated difference.

Application Example 3

A sensor control device according to Application example 2, wherein the difference calculation section includes an integrated value calculation section for obtaining an integrated value of the difference over a predetermined period; and the anomaly determination section determines that an anomaly has occurred when the integrated value becomes equal to or greater than a predetermined value.

Application Example 4

A sensor control device according to Application example 3, wherein the equivalent value acquisition section is configured to acquire the first characteristic equivalent value and the second characteristic equivalent value at predetermined intervals shorter than the predetermined period; the difference calculation section is configured to obtain, at the predetermined intervals, an integrated value of the difference by integrating a plurality of values of the difference between the first characteristic equivalent value and the second characteristic equivalent value acquired by the equivalent value acquisition section, the plurality of values being obtained through continuous sampling up to the present; and the anomaly determination section determines that an anomaly has occurred when the integrated value calculated by the difference calculation section becomes equal to or greater than a predetermined value.

Application Example 5

A sensor control device according to any one of Application examples 1 to 4, wherein the second detection range is narrower than the first detection range; and the second amplification factor is greater than the first amplification factor.

Application Example 6

A sensor control device according to any one of Application examples 1 to 5, comprising a plurality of amplification circuits which receive the electric signal value output from the sensor section, wherein one of the amplification circuits constitutes the first amplification section which amplifies the electric signal value at the first amplification factor, and another of the amplification circuits constitutes the second amplification section which amplifies the electric signal value at the second amplification factor.

Application Example 7

A sensor control device according to any one of Application examples 1 to 5, comprising an amplification circuit which receives the electric signal value output from the sensor section, wherein the amplification factor of the amplification circuit can be switched between the first amplification factor and the second amplification factor, the first amplification section is constituted when the amplification factor of the amplification circuit is set to the first amplification factor, and the second amplification section is constituted when the amplification factor of the amplification circuit is set to the second amplification factor.

Application Example 8

A sensor control device according to any one of Application examples 1 to 7, wherein the characteristic is the concentration of a specific gas contained in the measurement subject.

Application Example 9

A sensor control method which uses a sensor section which outputs an electric signal value corresponding to a physical or chemical characteristic of a measurement subject, a first amplification section which receives the electric signal value output from the sensor section and amplifies the electric signal value at a first amplification factor for a first detection range of the characteristic, and a second amplification section which receives the electric signal value output from the sensor section and amplifies the electric signal value at a second amplification factor for a second detection range of the characteristic, at least a portion of the second detection range overlapping with the first detection range, the method obtaining a value representing the characteristic on the basis of an output from the first amplification section and an output from the second amplification section, and outputting the value as a sensor detection value. The sensor control method is characterized by comprising an equivalent value acquisition step of acquiring a first characteristic equivalent value based on the output from the first amplification section and a second characteristic equivalent value based on the output from the second amplification section; a determination step of determining whether or not at least one of the first and second characteristic equivalent values falls within an anomaly diagnosis range, which is a predetermined range contained in an overlap portion between the first detection range and the second detection range; and an anomaly diagnosis step of determining, through comparison between the first characteristic equivalent value and the second characteristic equivalent value, whether or not an anomaly has occurred in at least one of a signal system containing the first amplification section and a signal system containing the second amplification section, when it is determined in the determination step that at least one of the first and second characteristic equivalent values falls within an anomaly diagnosis range.

Moreover, the present invention can be realized in the form of a computer program in which the steps of the sensor control method of the Application example 9 are realized by respective steps of the computer program. Also, the present invention can be realized, for example, in the form of a recording medium on which this computer program is recorded or a data signal which includes the computer program and is carried by a carrier wave.

Effects of the Invention

According to the sensor control device of Application example 1, a value showing the physical or chemical characteristic of a measurement subject is obtained on the basis of the output from the first amplification section and the output from the second amplification section. The "the physical or chemical characteristic" refers to a physical quantity or chemical quantity of the measurement subject. Furthermore, since a state in which at least one of the two characteristic equivalent values assumes an anomalous value can be detected through comparison between the first characteristic equivalent value based on the output of the first amplification section and the second characteristic equivalent value based on the output of the second amplification section, a determination can be made as to whether or not an anomalous has occurred in at least one of the signal system including the first amplification section and the signal system including the second amplification section. Accordingly, it is possible to accurately diagnose or detect a failure in which an input signal from an amplification circuit assumes an anomalous value in the intermediate range.

According to the sensor control device of Application example 2, the accuracy of the fault diagnosis can be improved further through use of the difference between the first characteristic equivalent value and the second characteristic equivalent value.

According to the sensor control device of Application example 3, the accuracy of the fault diagnosis can be improved further through use of the integrated value of the difference over a predetermined period.

According to the sensor control device of Application example 4, since the integrated value of the difference obtained by integrating a plurality of values of the difference continuously sampled up to the present is updated at predetermined intervals, anomaly determination can be performed without fail even in the case where the input signals from the amplification sections have periodicity.

According to the sensor control device of Application example 5, the input signal from the first amplification section having a relatively low amplification factor can represent a variation in a wide range, and the input signal from the second amplification section having a relatively high amplification factor can represent a variation in a narrow range. Therefore, in the case where the characteristic is desired to be detected in a wide range, in the control section, the input signal from the first amplification section is employed, whereby rough detection (with low resolution) can be performed. Meanwhile, the characteristic is desired to be detected with pinpoint accuracy, the input signal from the second amplification section is employed, whereby detection can be performed with high resolution.

Through application of the present invention to the sensor control device of Application example 6 including a plurality of amplification circuits which constitute the first amplification section and the second amplification section, it is possible to accurately determine, through diagnosis, whether or not an anomaly has occurred at least one of the signal system including the first amplification section and the signal system including the second amplification section.

The present invention can also be applied to the sensor control device of Application example 7, which differs from that of Application example 6 in the specific configuration of the first amplification section and the second amplification section. The sensor control device of Application example 7 includes an amplification circuit which constitutes the first amplification section or the second amplification section through switching of the amplification factor of the amplification circuit itself. In this case as well, there can be attained various effects, such as accurate diagnosis for determining whether or not an anomaly has occurred at least one of the signal system including the first amplification section and the signal system including the second amplification section.

According to the sensor control device of Application example 8, detection of the concentration of a specific gas becomes possible.

The sensor control method according to Application example 9 provides an action and effect similar to those provided by the sensor control device of Application example 1.

MODE FOR CARRYING OUT THE INVENTION

A mode of the present invention will next be described on the basis of embodiments, while referring to the drawings.

A. First Embodiment

A-1. Overall Configuration

Figure 1:
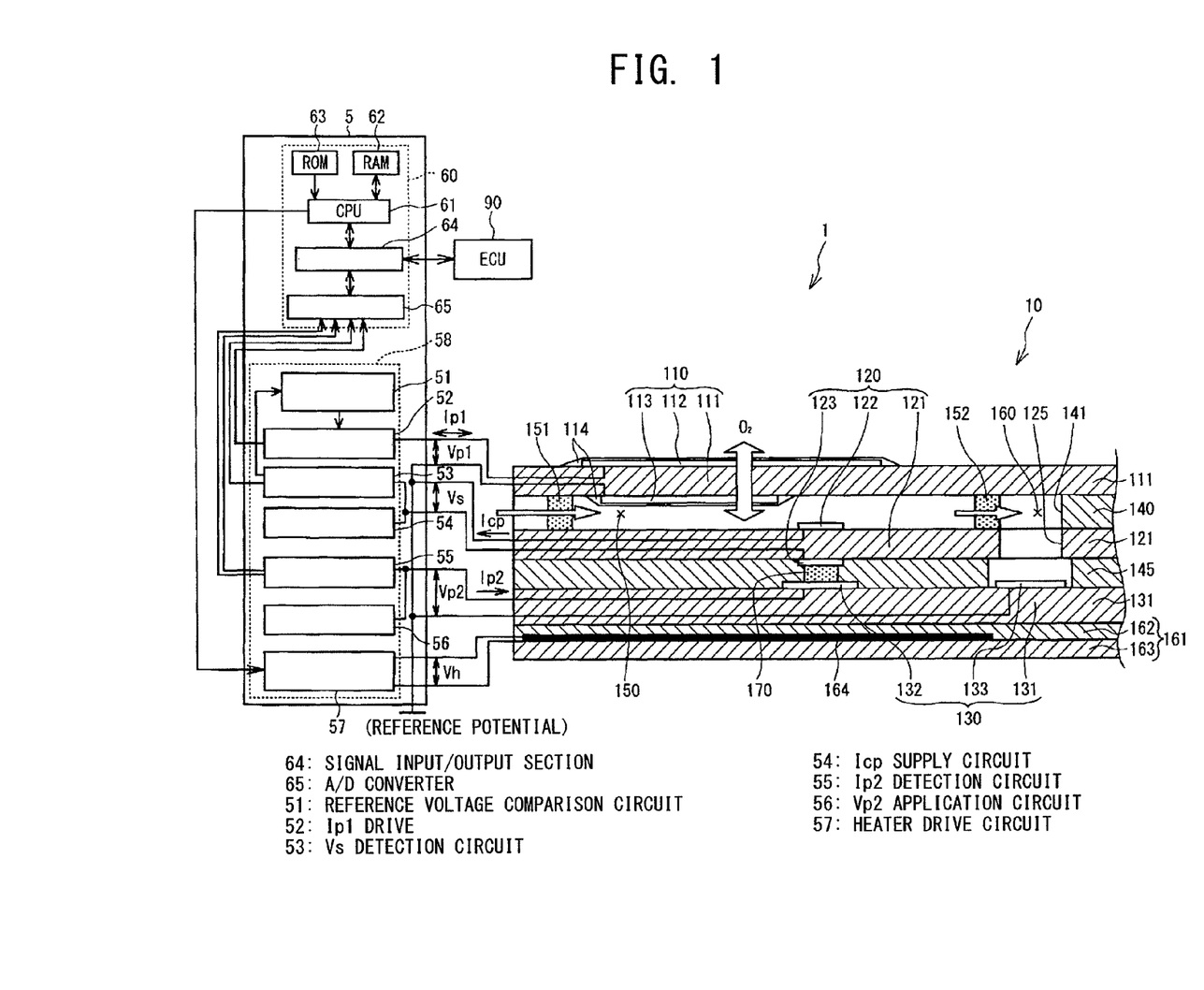
FIG. 1 Schematic diagram showing a sensor control device 5 according to a first embodiment of the present invention, and its periphery.

FIG. 1 is a schematic diagram showing a sensor control device 5 according to a first embodiment of the present invention, and its periphery. Reference numeral 1 in FIG. 1 denotes a gas sensor, and the sensor control device 5 is connected to the gas sensor 1. The gas sensor 1 includes a sensor element 10. The sensor element 10 is shown by a cross sectional view which shows its internal structure at a front end side portion thereof. The left side of FIG. 1 corresponds to the front end side of the sensor element 10.

The gas sensor 1 is disposed in an exhaust passage (not shown) to which exhaust gas of an internal combustion engine is discharged. The gas sensor 1 is used for exhaust gas of the internal combustion engine (measurement subject); specifically, is used to detect the $NO_X$ concentration of the exhaust gas (chemical quantity of the measurement subject). The gas sensor 1 includes the sensor element 10 having the shape of an elongated plate, and a housing (not shown) for attaching the gas sensor 1 to the exhaust passage. The sensor element 10 is held within the housing. Signal lines for carrying a signal output from the sensor element 10 are extended from the gas sensor 1, and electrically connected to the sensor control device 5, which is attached at a position away from the gas sensor 1.

Next, the structure of the sensor element 10 will be described. The sensor element 10 is configured such that three plate-like solid electrolyte members 111, 121, and 131 are arranged in layers with insulators 140 and 145 of alumina or the like intervening therebetween. A heater element 161 is provided on the external side (lower side in FIG. 1) of the solid electrolyte member 131. The heater element 161 includes laminated sheet-like insulating layers 162 and 163, which contain a predominant amount of alumina, and a heater pattern 164, which contains a predominant amount of Pt and is embedded between the insulating layers 162 and 163.

The solid electrolyte members 111, 121, and 131 are formed from zirconia, which is a solid electrolyte, and have oxygen-ion conductivity. Porous electrodes 112 and 113 are provided on respective opposite surfaces of the solid electrolyte member 111 with respect to the direction of lamination of the sensor element 10 such that the electrodes 112 and 113 sandwich the solid electrolyte member 111. The electrodes 112 and 113 are formed from Pt, a Pt alloy, cermet which contains Pt and ceramic, or a like material. A porous protective layer 114 of ceramic is formed on the surface of each of the electrodes 112 and 113 for protecting the electrodes 112 and 113 from deterioration, which could otherwise result from exposure to a poisoning gas contained in exhaust gas (a reducing atmosphere).

By causing a current to flow between the electrodes 112 and 113, the solid electrolyte member 111 can pump oxygen out or in (so-called oxygen pumping) between an atmosphere in contact with the electrode 112 (atmosphere externally of the sensor element 10) and an atmosphere in contact with the electrode 113 (atmosphere in a first measurement chamber 150, which will be described later). In the present embodiment, the solid electrolyte member 111 and the electrodes 112 and 113 are collectively called an Ip1 cell 110.

The solid electrolyte member 121 is disposed in such a manner as to face the solid electrolyte member 111 with the insulator 140 intervening therebetween. As in the case of the solid electrolyte member 111, porous electrodes 122 and 123 are provided on respective opposite surfaces of the solid electrolyte member 121 with respect to the direction of lamination of the sensor element 10, such that the electrodes 122 and 123 sandwich the solid electrolyte member 121. The electrodes 122 and 123 are provided on one side of the first measurement chamber 150 toward the solid electrolyte member 121 such that the electrode 122 is located inside the first measurement chamber 150, and the electrode 123 is located outside the first measurement chamber 150. The electrodes 122 and 123 are formed from Pt, a Pt alloy, cermet which contains Pt and ceramic, or a like material. The electrode 122 is formed on a side facing the solid electrolyte member 111.

A small space serving as the first measurement chamber 150 is formed between the solid electrolyte member 111 and the solid electrolyte member 121. The first measurement chamber 150 is a small space within the sensor element 10 into which exhaust gas flowing through the exhaust passage is first introduced. The electrode 113 on the solid electrolyte member 111 and the electrode 122 on the solid electrolyte member 121 are disposed in the first measurement chamber 150. A first diffusion resistance portion 151 formed of porous ceramic is provided in the first measurement chamber 150 at a position located toward the front end of the sensor element 10; serves as a partition between the interior and the exterior of the first measurement chamber 150; and is adapted to limit inflow per unit time of the exhaust gas into the first measurement chamber 150. Similarly, a second diffusion resistance portion 152 formed of porous ceramic is provided in the first measurement chamber 150 at a position located toward the rear end of the sensor element 10; serves as a partition between the first measurement chamber 150 and an opening portion 141 communicating with a second measurement chamber 160, which will be described later; and is adapted to limit flow per unit time of the exhaust gas.

The two electrodes 122 and 123 generate electromotive force according to the difference in partial pressure of oxygen between atmospheres (an atmosphere in the first measurement chamber 150 and in contact with the electrode 122 and an atmosphere in a reference-oxygen chamber 170, which will be described later, and in contact with the electrode 123) separated from each other by the solid electrolyte member 121. In the present embodiment, the solid electrolyte member 121 and the two electrodes 122 and 123 are collectively called an oxygen concentration detection cell (hereinafter referred as the "Vs cell") 120. That is, the Vs cell 120 has the electrode 122 provided inside the first measurement chamber 150, and the electrode 123 provided outside the first measurement chamber 150.

The solid electrolyte member 131 is disposed in such a manner as to face the solid electrolyte member 121 with the insulator 145 intervening therebetween. Porous electrodes 132 and 133 are provided on the solid electrolyte layer 131 on a side toward the solid electrolyte layer 121 such that they are separated from each other. The porous electrodes 132 and 133 are formed from Pt, a Pt alloy, cermet which contains Pt and ceramic, or a like material.

The reference-oxygen chamber 170, which is formed between the solid electrolyte members 131 and 121 and in which the insulator 145 is absent, is an independent small space. The electrode 132 and the electrode 123 of the Vs cell 120 are disposed in the reference-oxygen chamber 170. The space of the reference-oxygen chamber 170 sandwiched between the electrode 132 and the electrode 123 of the Vs cell 120 is filled with a porous body of ceramic.

The second measurement chamber 160, which is formed between the solid electrolyte members 131 and 111 and in which the insulator 145 is absent, is an independent small space. The second measurement chamber 160 is separated from the reference-oxygen chamber 170 by the insulator 145. An opening portion 125 and the opening portion 141 are provided in the solid electrolyte member 121 and the insulator 140, respectively, in such a manner as to communicate with the second measurement chamber 160. As mentioned previously, the first measurement chamber 150 and the opening portion 141 are connected to each other with the second diffusion resistance portion 152 intervening therebetween.

As in the case of the above-mentioned Ip1 cell 110, the solid electrolyte member 131 and the two electrodes 132 and 133 can cooperatively pump out oxygen between atmospheres (an atmosphere in the reference oxygen chamber 170 to which the electrode 132 is exposed and an atmosphere in the second measurement chamber 160 to which the electrode 133 is exposed) separated from each other by the insulator 145. In the present embodiment, the solid electrolyte member 131 and the two electrodes 132 and 133 are collectively called an Ip2 cell 130. The electrode 113 of the Ip1 cell 110 located on the side toward the first measurement chamber 150, the electrode 122 of the Vs cell 120 located on the side toward the first measurement chamber 150, and the electrode 133 of the Ip2 cell 130 located on the side toward the second measurement chamber 160 are connected to a reference potential.

Next, the configuration of the sensor control device 5 will be described. The sensor control device 5 is electrically connected to the sensor element 10 of the gas sensor 1. The sensor control device 5 is mainly composed of a microcomputer 60 and an electric circuit section 58.

The microcomputer 60 includes a CPU 61 having a known structure, RAM 62, ROM 63, a signal input/output section 64, an A/D converter 65, and an unillustrated timer clock. The CPU 61 communicates with the RAM 62 and the ROM 63, communicates with the ECU 90 via the signal input/output section 64, and communicates with the electric circuit section 58 via the signal input/output section 64 and the A/D converter 65. For example, information regarding the supply of fuel to an internal combustion engine is provided from the ECU 90 to the microcomputer 60.

The electric circuit section 58 includes a reference voltage comparison circuit 51, an Ip1 drive circuit 52, a Vs detection circuit 53, an Icp supply circuit 54, an Ip2 detection circuit 55, a Vp2 application circuit 56, and a heater drive circuit 57. Under the control by the microcomputer 60, the electric circuit section 58 detects the $NO_X$ concentration of exhaust gas by use of the sensor element 10 of the gas sensor 1.

The Icp supply circuit 54 supplies current Icp which flows between the electrodes 122 and 123 of the Vs cell 120 for pumping out oxygen from the first measurement chamber 150 into the reference-oxygen chamber 170. The Vs detection circuit 53 is adapted to detect voltage Vs between the electrodes 122 and 123, and outputs the detected voltage to the reference voltage comparison circuit 51. The reference voltage comparison circuit 51 is adapted to compare the voltage Vs detected by the Vs detection circuit 53 with a reference voltage (e.g., 425 mV) and outputs the result of the comparison to the Ip1 drive circuit 52.

The Ip1 drive circuit 52 is adapted to supply current Ip1 which flows between the electrodes 112 and 113 of the Ip1 cell 110. The Ip1 drive circuit 52 adjusts the magnitude and direction of the current Ip1, on the basis of the result of comparison between the previously set reference voltage and the voltage Vs between the electrodes 122 and 123 of the Vs cell 120 performed by the reference voltage comparison circuit 51, such that the voltage Vs substantially coincides with the reference voltage. As a result, the Ip1 cell 110 pumps out oxygen from the first measurement chamber 150 to the exterior of the sensor element 10 or pumps oxygen into the first measurement chamber 150 from the exterior of the sensor element 10. In other words, as a result of electricity supply control by the Ip1 drive circuit 52, the Ip1 cell 110 adjusts the oxygen concentration within the first measurement chamber 150 such that the voltage between the electrodes 122 and 123 of the Vs cell 120 is maintained at a constant value (the value of the reference voltage).

The Vp2 application circuit 56 is adapted to apply a predetermined voltage Vp2 (e.g., 450 mV) between the electrodes 132 and 133 of the Ip2 cell 130, whereby oxygen is pumped out from the second measurement chamber 160 into the reference-oxygen chamber 170. The Ip2 detection circuit 55 is adapted to detect current Ip2 flowing from the electrode 133 to the electrode 132 of the Ip2 cell 130.

The heater drive circuit 57 is adapted to maintain the temperatures of the solid electrolyte members 111, 121, and 131 at a predetermined temperature. The heater drive circuit 57 is controlled by the CPU 61 and is adapted to supply current to the heater pattern 164 of the heater element 161, to thereby heat the solid electrolyte members 111, 121, and 131 (in other words, the Ip1 cell 110, the Vs cell 120, and the Ip2 cell 130). The heater pattern 164 is a single electrode pattern extending in the heater element 161. One end of the heater pattern 164 is grounded, and the other end thereof is connected to the heater drive circuit 57. The heater drive circuit 57 controls the supply of electricity to the heater pattern 164 through PWM control to thereby control the current flowing through the heater pattern 164 such that the solid electrolyte members 111, 121, and 131 are heated to a target temperature.

The sensor control device 5 having the above-described configuration detects the $NO_X$ concentration of exhaust gas through use of the sensor element 10 of the gas sensor 1. Next, operation of detecting the $NO_X$ concentration by making use of the gas sensor 1 will be described.

As the temperature of the heater pattern 164 increases as a result of supply of drive current thereto from the heater drive circuit 57, the solid electrolyte members 111, 121, and 131 constituting the sensor element 10 of the gas sensor 1 are heated and thus activated. By this procedure, the Ip1 cell 110, the Vs cell 120, and the Ip2 cell 130 become operable.

The exhaust gas flowing through the exhaust passage (not shown) is introduced into the first measurement chamber 150 while its flow rate is limited by the first diffusion resistance portion 151. Meanwhile, the Icp supply circuit 54 supplies the current Icp which flows through the Vs cell 120 from the electrode 123 to the electrode 122. Thus, oxygen contained in the exhaust gas can receive electrons from the electrode 122 of negative polarity located in the first measurement chamber 150, thereby becoming oxygen ions. The oxygen ions flow through the solid electrolyte member 121 and move into the reference-oxygen chamber 170. That is, as a result of the current Icp flowing between the electrodes 122 and 123, oxygen contained in the first measurement chamber 150 is fed into the reference-oxygen chamber 170.

The Vs detection circuit 53 detects the voltage Vs between the electrodes 122 and 123. The reference voltage comparison circuit 51 compares the detected voltage Vs with the reference voltage (e.g., 425 mV). The result of the comparison is output to the Ip1 drive circuit 52. By means of adjusting the oxygen concentration within the first measurement chamber 150 such that the difference in electric potential between the electrodes 122 and 123 is maintained at a constant value around 425 mV, the oxygen concentration of the exhaust gas contained in the first measurement chamber 150 approaches a predetermined value (e.g., $10^{-8}$ atm to $10^{-9}$ atm).

In the case where the oxygen concentration of the exhaust gas introduced into the first measurement chamber 150 is lower than the predetermined value, the Ip1 drive circuit 52 supplies the current Ip1 to the Ip1 cell 110 such that the electrode 112 assumes negative polarity, so as to pump oxygen into the first measurement chamber 150 from the exterior of the sensor element 10. By contrast, in the case where the oxygen concentration of the exhaust gas introduced into the first measurement chamber 150 is higher than the predetermined value, the Ip1 drive circuit 52 supplies the current Ip1 to the Ip1 cell 110 such that the electrode 113 assumes negative polarity, so as to pump out oxygen from the first measurement chamber 150 to the exterior of the sensor element 10. The oxygen concentration of exhaust gas can be detected from the magnitude and flow direction of the current Ip1 at that time.

The exhaust gas whose oxygen concentration has been adjusted in the first measurement chamber 150 is introduced into the second measurement chamber 160 via the second diffusion resistance portion 152. In the second measurement chamber 160, $NO_X$ contained in the exhaust gas comes into contact with the electrode 133 and is decomposed (reduced) into $N_2$ and $O_2$ by the catalytic effect of the electrode 133. Oxygen generated through decomposition receives electrons from the electrode 133, thereby becoming oxygen ions. The oxygen ions flow through the solid electrolyte member 131 and move into the electrode 123 (the reference oxygen chamber 170). Since the Ip2 current corresponding to the amount of oxygen ions flowing through the solid electrolyte member 131; i.e., the Ip2 current flowing through the Ip2 cell 130, is approximately proportional to the $NO_X$ concentration, the $NO_X$ concentration can be detected on the basis of the Ip2 current.

A-2. Configuration of the Ip2 Detection Circuit

Figure 2:
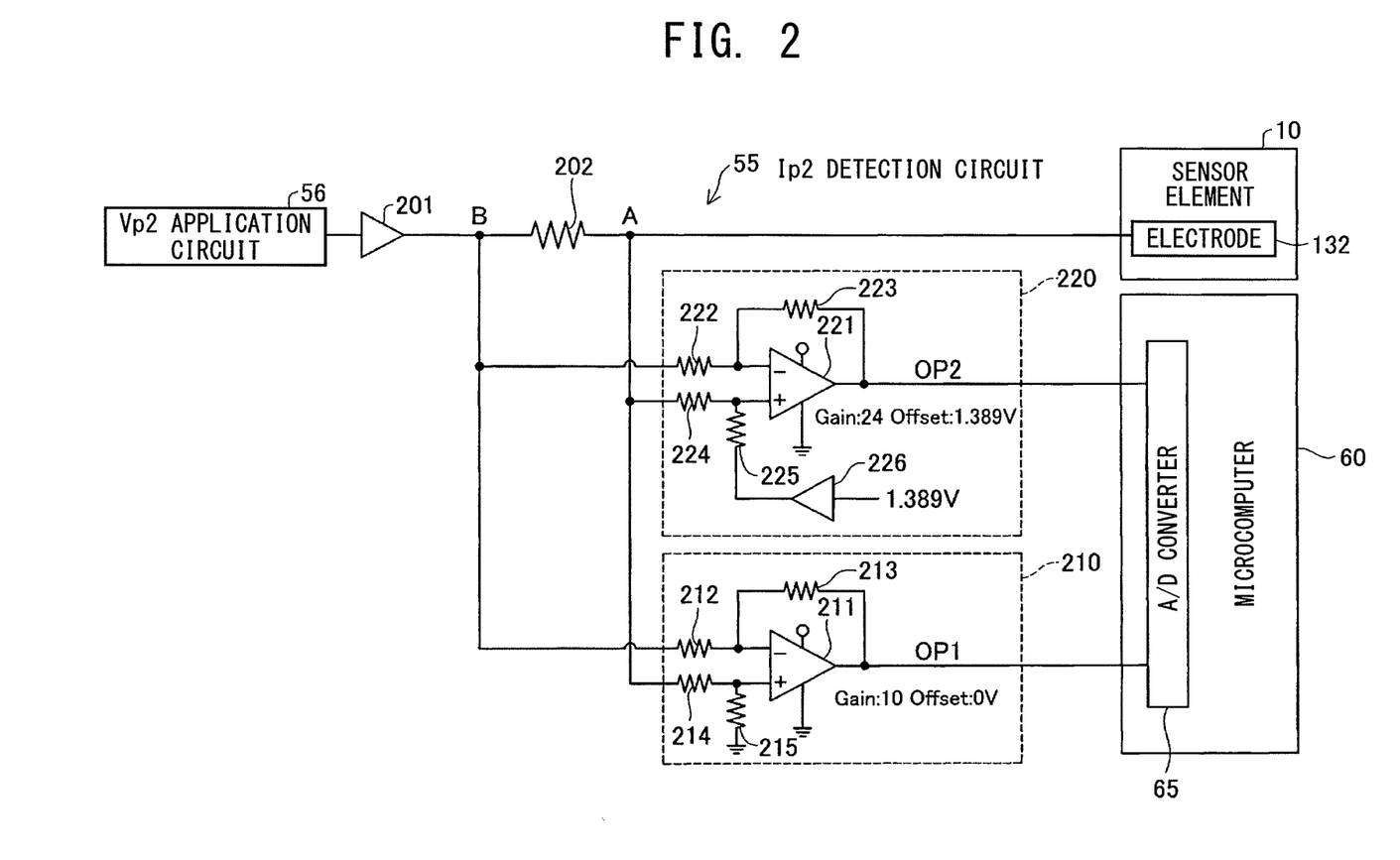
FIG. 2 Diagram showing the circuit configuration of an Ip2 detection circuit 55.

As described above, the Ip2 detection circuit 55 is a circuit for detecting the value of the current Ip2 flowing from the electrode 133 to the electrode 132 of the Ip2 cell 130. In the present embodiment, the value of the current Ip2 is detected as two values. Next, the detailed circuit diagram of the Ip2 detection circuit 55 will be described.

FIG. 2 is a diagram showing the configuration of the Ip2 detection circuit 55. As shown in FIG. 2, the above-described Vp2 application circuit 56 is connected to the electrode 132 (the positive side terminal) of the sensor element 10 via the buffer 201 and the current detection resistor 202.

The first differential amplification circuit 210 and the second differential amplification circuit 220 are connected to points A and B, respectively, located at opposite ends of the current detection resistor 202. The outputs OP1 and OP2 of the first and second differential amplification circuits 210 and 220 are input to the microcomputer 60. Notably, the sensor element 10 and the current detection resistor 202 correspond to the "sensor section" in Application example 1.

The first and second differential amplification circuits 210 and 220 are connected in parallel. Each of the first and second differential amplification circuits 210 and 220 has a known configuration. The first differential amplification circuit 210 includes an operational amplifier 211 and four resistors 212 to 215. Similarly, the second differential amplification circuit 220 includes an operational amplifier 221 and four resistors 222 to 225. Notably, a voltage of 1.389 V is applied to the +input pin of the operational amplifier 221 of the second differential amplification circuit 220 via the resistor 225 and a buffer 226. The operational amplifiers 211 and 221 are driven by a constant drive voltage (e.g., 5 V) obtained from a battery power supply through step-down conversion.

The first differential amplification circuit 210 having the above-described configuration has an amplification factor (gain) of 10 and no offset. The second differential amplification circuit 220 having the above-described configuration has an amplification factor of 24 and an offset of 1.389 V. The outputs OP1 and OP2 of the first and second differential amplification circuits 210 and 220 (voltage signals representing the current flowing through the sensor element 10) are input to the A/D converter 65 of the microcomputer 60.

Since the output OP1 of the first differential amplification circuit 210 falls within the range of operation voltage (e.g., 0 to 5 V) of the A/D converter 65 when the $NO_X$ concentration falls within a predetermined wide range (e.g., 0 to 700 ppm), the first differential amplification circuit 210 can output a proper signal in the wide range. Meanwhile, since the output OP2 of the second differential amplification circuit 220 falls within the range of operation voltage of the A/D converter 65 when the $NO_X$ concentration falls within a predetermined narrow range (e.g., −100 to 200 ppm), the second differential amplification circuit 220 can output a proper signal in the narrow range.

Notably, the above-mentioned "wide range" corresponds to the "first detection range" in Application example 1, and the first differential amplification circuit 210 corresponds to the "first amplification section" in Application example 1. Also, the above-mentioned "narrow range" corresponds to the "second detection range" in Application example 1, and the second differential amplification circuit 220 corresponds to the "second amplification section" in Application example 1.

A-3. Detection of $NO_X$ Concentration

Referring back to FIG. 1, the CPU 61 of the microcomputer 60 receives first and second digital signals output from the A/D converter 65; i.e., the A/D converted values of the outputs OP1 and OP2 of the first and second differential amplification circuits 210 and 220, and calculates the $NO_X$ concentration ($NO_X$ concentration equivalent value) on the basis of an A/D converted value selected from the two A/D converted values. Specifically, the CPU 61 obtains a first $NO_X$ concentration ($NO_X$ concentration equivalent value) by multiplying the A/D converted value of the output OP1 of the first differential amplification circuit 210 by a predetermined value (a constant determined depending on the sensor element 10). When this first $NO_X$ concentration does not fall within the above-mentioned narrow range, the CPU 61 outputs the first $NO_X$ concentration as a final value of the $NO_X$ concentration detected by the sensor. Meanwhile, when the first $NO_X$ concentration falls within the above-mentioned narrow range, the CPU 61 obtains a second $NO_X$ concentration ($NO_X$ concentration equivalent value) by multiplying the A/D converted value of the output OP2 of the second differential amplification circuit 220 by the above-mentioned predetermined value, and outputs the second $NO_X$ concentration as the final value of the $NO_X$ concentration detected by the sensor.

By virtue of this $NO_X$ concentration calculation processing, when the $NO_X$ concentration is desired to be detected with pinpoint accuracy (in other words, the $NO_X$ concentration is desired to be accurately detected on the low concentration side), detection of high resolution becomes possible through employment of the A/D converted value of the output OP2 of the second differential amplification circuit 220. Notably, the microcomputer 60 and the $NO_X$ concentration calculation processing executed by the CPU 61 of the microcomputer 60 correspond to the "control section" of Application example 1.

A-4. Anomaly Diagnosis

The microcomputer 60 provided in the sensor control device 5 having the above-described configuration further performs anomaly diagnosis for the sensor control device 5. This anomaly diagnosis will now be described in detail.

Figure 3:
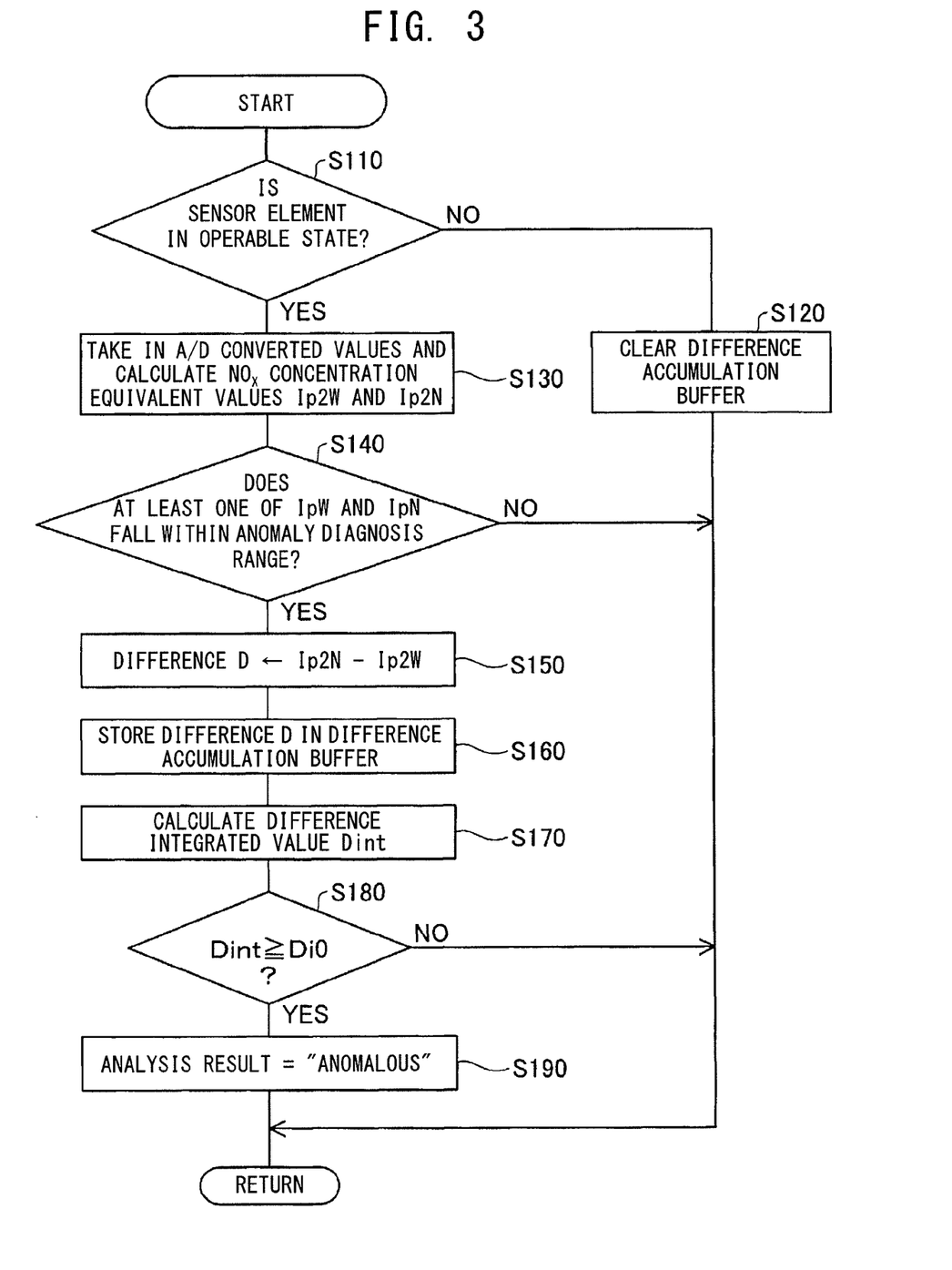
FIG. 3 Flowchart showing anomaly diagnosis processing executed by a microcomputer 60.

FIG. 3 is a flowchart showing anomaly diagnosis processing executed by the CPU 61 of the microcomputer 60. This anomaly diagnosis processing is repeatedly executed at predetermined intervals. When the processing is started, the CPU 61 first determines whether or not the sensor element 10 is in an operable state (a state in which the sensor element 10 can sense the $NO_X$ concentration) (step S110). Specifically, the CPU 61 determines whether or not the sensor element 10 is in the operable state by determining whether or not all the requirements (such as the temperature of the solid electrolyte members 111, 121, and 131 of the sensor element 10 being equal to or greater than a predetermined value, and the power supply voltage of the sensor element 10 being equal to or greater than a predetermined value) are satisfied.

When the CPU 61 determines in step S110 that the sensor element 10 is not in the operable state, the CPU 61 clears a previously prepared difference accumulation buffer (step S120), and then returns to the base routine to thereby end the current execution of this anomaly diagnosis processing. Notably, the difference accumulation buffer will be described later.

Meanwhile, when the CPU 61 determines in step S110 that the sensor element 10 is in the operable state, the CPU 61 takes in the first and second digital signals output from the A/D converter 65; i.e., the A/D converted values of the outputs OP1 and OP2 of the first and second differential amplification circuits 210 and 220. Subsequently, the CPU 61 obtains a first $NO_X$ concentration ($NO_X$ concentration equivalent value) Ip2W by multiplying the A/D converted value of the output OP1 by a predetermined value, and obtains a second $NO_X$ concentration ($NO_X$ concentration equivalent value) Ip2N by multiplying the A/D converted value of the output OP2 by the predetermined value (step S130). Notably, the predetermined value is a constant previously determined depending on the sensor element 10.

Figure 4:
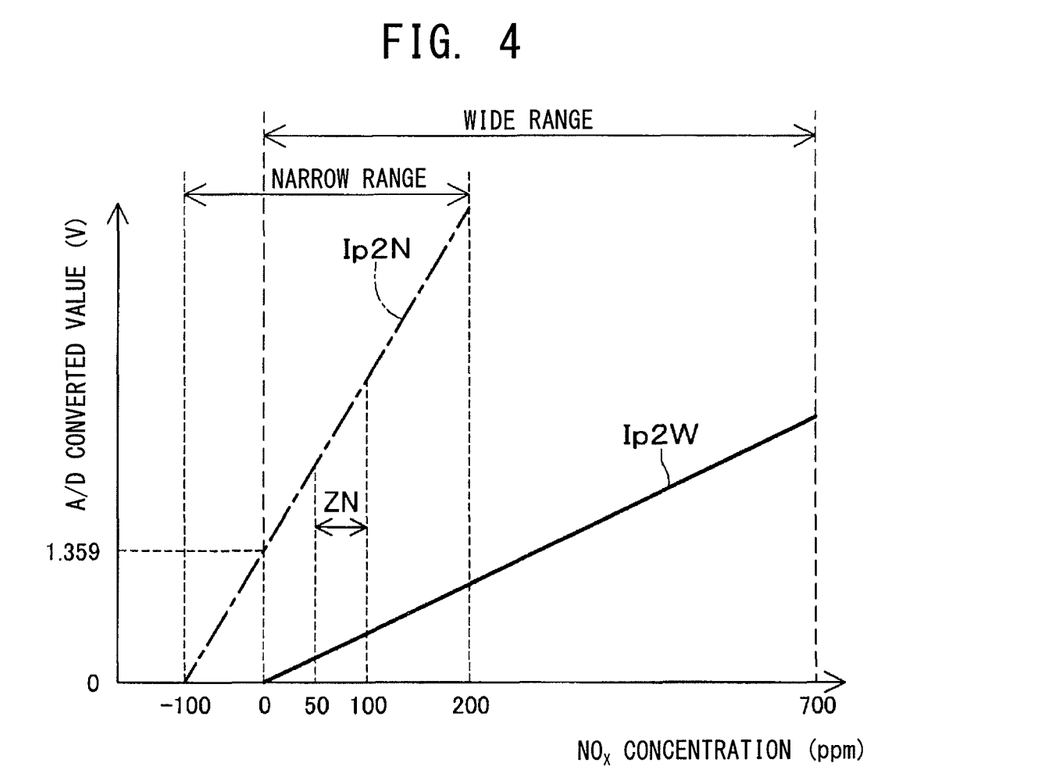
FIG. 4 Graph showing first and second $NO_X$ concentrations Ip2W, Ip2N for A/D converted value.

FIG. 4 is a graph showing the relation between the A/D converted value and the first and second $NO_X$ concentrations Ip2W and Ip2N. The vertical axis of the graph represents the A/D converted values of the outputs OP1 and OP2 of the first and second differential amplification circuits 210 and 220, and the horizontal axis of the graph represents the $NO_X$ concentration. A continuous line in the graph shows the first $NO_X$ concentration Ip2W, and an alternating long and short dash line in the graph shows the second $NO_X$ concentration Ip2N. As shown in the graph, the first $NO_X$ concentration Ip2W for the wide range is obtained through amplification in which the amplification factor is set to 10 and the offset is set to 0 V, and the second $NO_X$ concentration Ip2N for the narrow range is obtained through amplification in which the amplification factor is set to 24 and the offset is set to 1.389 V.

Referring back to FIG. 3, after execution of step S130, the CPU 61 determines whether or not at least one of the first and second $NO_X$ concentrations Ip2W and Ip2N falls within an anomaly diagnosis range ZN (step S140). As shown in FIG. 4, the anomaly diagnosis range ZN is a predetermined range contained in an overlapping portion between the wide range determined based on the output OP1 of the first differential amplification circuit 210, and the narrow range determined based on the output OP2 of the second differential amplification circuit 220. In the present embodiment, the anomaly diagnosis range ZN is 50 to 100 ppm. In the case where the CPU 61 determines in step S140 that none of the first and second $NO_X$ concentrations Ip2W and Ip2N falls within the anomaly diagnosis range ZN, the CPU 61 returns to the base routine so as to end the current execution of the processing.

Meanwhile, in the case where the CPU 61 determines in step S140 that at least one of the first and second $NO_X$ concentrations Ip2W and Ip2N falls within the anomaly diagnosis range ZN, the CPU 61 calculates a difference D by subtracting the first $NO_X$ concentration Ip2W from the second $NO_X$ concentration Ip2N (step S150). Notably, in the present embodiment, since each of the first and second $NO_X$ concentrations Ip2W and Ip2N is a value equivalent to the $NO_X$ concentration, no problem arises in the calculation of the difference D through subtraction of the second $NO_X$ concentration Ip2N from the first $NO_X$ concentration Ip2W. Subsequently, the CPU 61 stores, in the difference accumulation buffer, the difference D calculated in step S150 (step S160). The difference accumulation buffer is prepared in the RAM 62 (FIG. 1), and has the following configuration.

Figure 5:
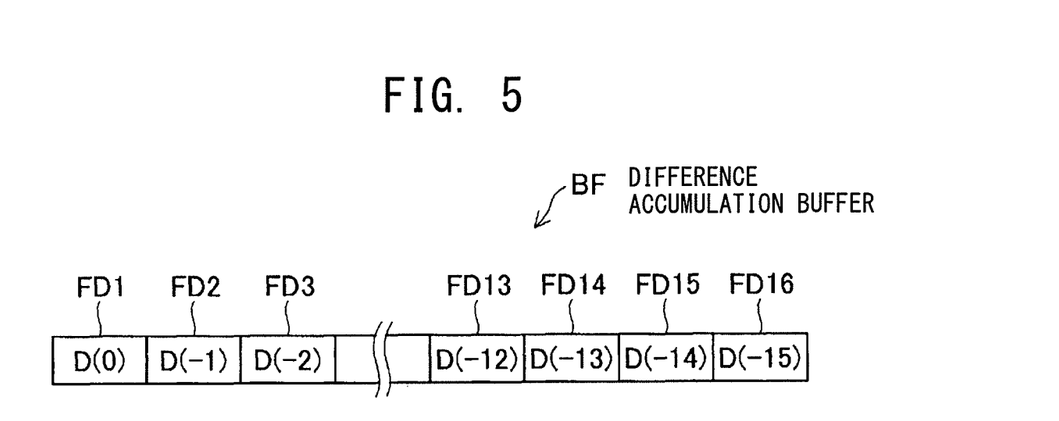
FIG. 5 Explanatory diagram showing a difference accumulation buffer BF.

FIG. 5 is an explanatory diagram showing the difference accumulation buffer BF. As shown in FIG. 5, the difference accumulation buffer BF has 16 fields FD1 to FD16, and can accumulate 16 differences D. The newest difference D(0) is stored in the leftmost field FD1; the differences D(-1), D(-2), ..., D(-14) of the older generations (the older sampled differences) are successively stored toward the right in the drawing; and the difference D(-15) calculated 15 generations ago is stored on the rightmost field FD16.

Every time the CPU 61 executes step S160 of FIG. 3, the CPU 61 shifts rightward the differences stored in the fields FD1 to FD15 by one field, and stores the difference D calculated in step S150 in the leftmost field FD1. As a result, the most recent 16 (sampled) differences D are stored in the difference accumulation buffer BF and updated at all times.

Subsequently, the CPU 61 adds together (integrate) the difference D of each generation stored in the difference accumulation buffer BF; i.e., the differences D(0) to D(-15), to thereby calculate a difference integrated value Dint (step S170). After that, the CPU 61 determines whether or not the difference integrated value Dint is equal to or greater than a predetermined value Di0 (step S180). The predetermined value Di0 is a constant previously determined in consideration of noise and circuit variation, and is, for example, 200 ppm.

In the case where the difference integrated value Dint is determined in step S180 to be equal or greater than the predetermined value Di0, the CPU 61 finally determines that the result of the diagnosis is "anomalous" (step S190). Notably, this diagnosis result is reported to the outside, for example, by sending the result to the ECU 90. After execution of step S190, the CPU 61 returns to the base routine so as to end the present execution of the present anomaly diagnosis processing. Meanwhile, in the case where the difference integrated value Dint is determined in step S180 to be less than the predetermined value Di0, the CPU 61 returns to the base routine so as to end the present execution of the present anomaly diagnosis processing, without execution of step S190; i.e., while maintaining that the result of the diagnosis is "normal."

In the above-described anomaly diagnosis processing, the CPU 61 and the processing of step S130 executed by the CPU 61 correspond to the "equivalent value acquisition section" in Application example 1. Also, the CPU 61 and the processing of step S140 executed by the CPU 61 correspond to the "equivalent value determination section" in Application example 1. The CPU 61 and the processing of step S150 or S190 executed by the CPU 61 correspond to the "anomaly diagnosis section" in Application example 1.

A-5. Effects of the Embodiment

As described in detail above, the sensor control device 5 of the first embodiment is configured such that, when at least one of the first $NO_X$ concentration Ip2W based on the output OP1 of the first differential amplification circuit 210 and the second $NO_X$ concentration Ip2N based on the output OP2 of the second differential amplification circuit 220 falls within the anomaly diagnosis range ZN, the sensor control device 5 obtains the difference D between the first $NO_X$ concentration Ip2W and the second $NO_X$ concentration Ip2N (in the present embodiment, the difference D=the second $NO_X$ concentration Ip2N−the first $NO_X$ concentration Ip2W); stores, in the difference accumulation buffer BF, 16 values of the difference D obtained though continuous sampling up to the present; obtains the integrated value (the difference integrated value) Dint of these values of the differences D; and determines that the result of the diagnosis is "anomalous" when the difference integrated value Dint becomes equal to or greater than the predetermined value Di0. When an anomaly (failure) occurs in at least one of a signal system including the first differential amplification circuit 210 and a signal system including the second differential amplification circuit 220, the difference D between the first $NO_X$ concentration Ip2W and the second $NO_X$ concentration Ip2N increases, and the difference integrated value Dint increases. Therefore, by means of determining whether or not the difference integrated value Dint becomes equal to or greater than the predetermined value Di0 as described above, it is possible to accurately diagnose or detect a failure in which the input signals from the differential amplification circuits 210 and 220 assume an anomalous value within the intermediate range.

Also, since the sensor control device 5 of the first embodiment uses the difference accumulation buffer BF, every time the first $NO_X$ concentration Ip2W and the second $NO_X$ concentration Ip2N are taken in, the difference integrated value Dint of the newest 16 values of the difference D can be obtained. Therefore, even in the case where the input signals from the differential amplification circuits 210 and 220 have periodicity, anomaly determination can be performed without fail.

B. Second Embodiment

Figure 6:
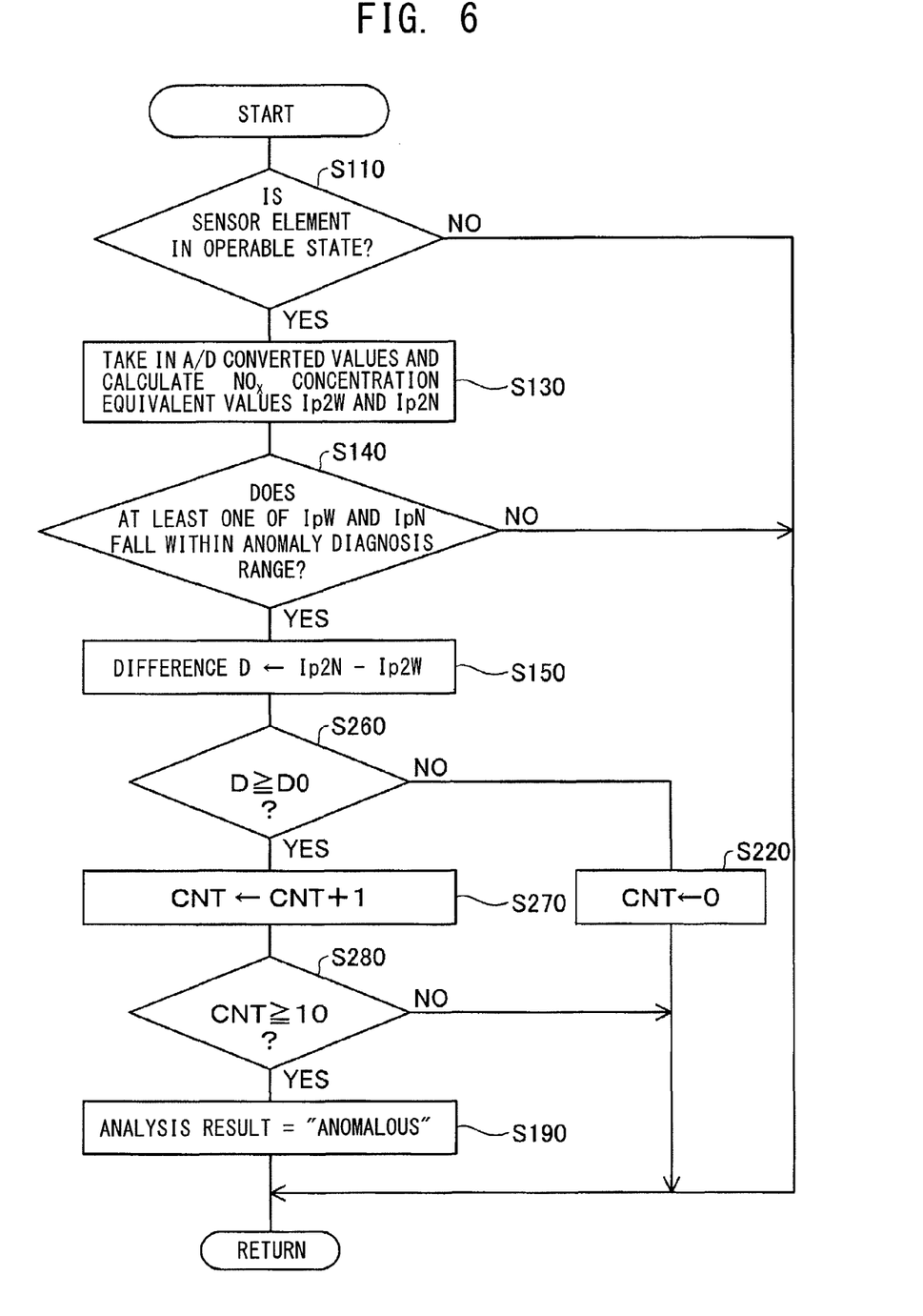
FIG. 6 Flowchart showing anomaly diagnosis processing executed in a sensor control device according to a second embodiment of the present invention.

FIG. 6 is a flowchart showing anomaly diagnosis processing executed in a sensor control device according to a second embodiment of the present invention. Although the sensor control device of the second embodiment differs from the sensor control device 5 of the first embodiment in the details of the anomaly diagnosis processing, the sensor control device of the second embodiment is identical with the sensor control device 5 in terms of the remaining portion of the software and the hardware configuration. This anomaly diagnosis processing corresponds to the processing shown in FIG. 3 of the first embodiment, and, as shown in FIG. 6, the CPU of the microcomputer executes the processing of steps S110, S130, S140, and S150, which are identical with those of the first embodiment.

After having calculated the difference D in step S150, the CPU determines whether or not the difference D is equal to or greater than a predetermined value D0 (step S260). The predetermined value D0 is determined in consideration of noise and circuit variation, and is, for example, 20 ppm. In the case where the CPU determines in step S260 that the difference D is equal to or greater than the predetermined value D0, the CPU increases a counter value CNT by an increment of 1 (step S270). The counter value CNT is used to count the number of times the difference D becomes equal to or greater than the predetermined value D0, and is cleared when the difference D is determined in step S260 to be less than the predetermined value D0 (step S220).

After the increment of the count value CNT in step S270, the CPU determines whether or not the count value CNT is equal to or greater than 10 (step S280). When the count value CNT is equal to or greater than 10, the CPU determines that the result of the analysis is "anomalous" (step S190). The processing of this step S190 is identical with that of the first embodiment. After that, the CPU returns to the base routine so as to end the current execution of this anomaly diagnosis processing. Meanwhile, when the CPU determines in step S280 that the count value CNT is less than 10, the CPU returns to the base routine so as to end the current execution of this anomaly diagnosis processing, without executing step S190.

Also, when the CPU determines in step S110 that the sensor element 10 is not in an operable state, the CPU returns to the base routine so as to end the current execution of this anomaly diagnosis processing.

Like the sensor control device of the first embodiment, the sensor control device of the second embodiment having the above-described configuration performs the anomaly diagnosis on the basis of the difference between the first $NO_X$ concentration Ip2W based on the output from the first differential amplification circuit and the second $NO_X$ concentration Ip2N based on the output from the second differential amplification circuit. Therefore, the sensor control device of the second embodiment achieves the same effect as that achieved by the sensor control device of the first embodiment. That is, the sensor control device of the second embodiment can accurately diagnose or detect a failure in which the input signals from the differential amplification circuits assume an anomalous value within the intermediate range.

C. Third Embodiment

Figure 7:
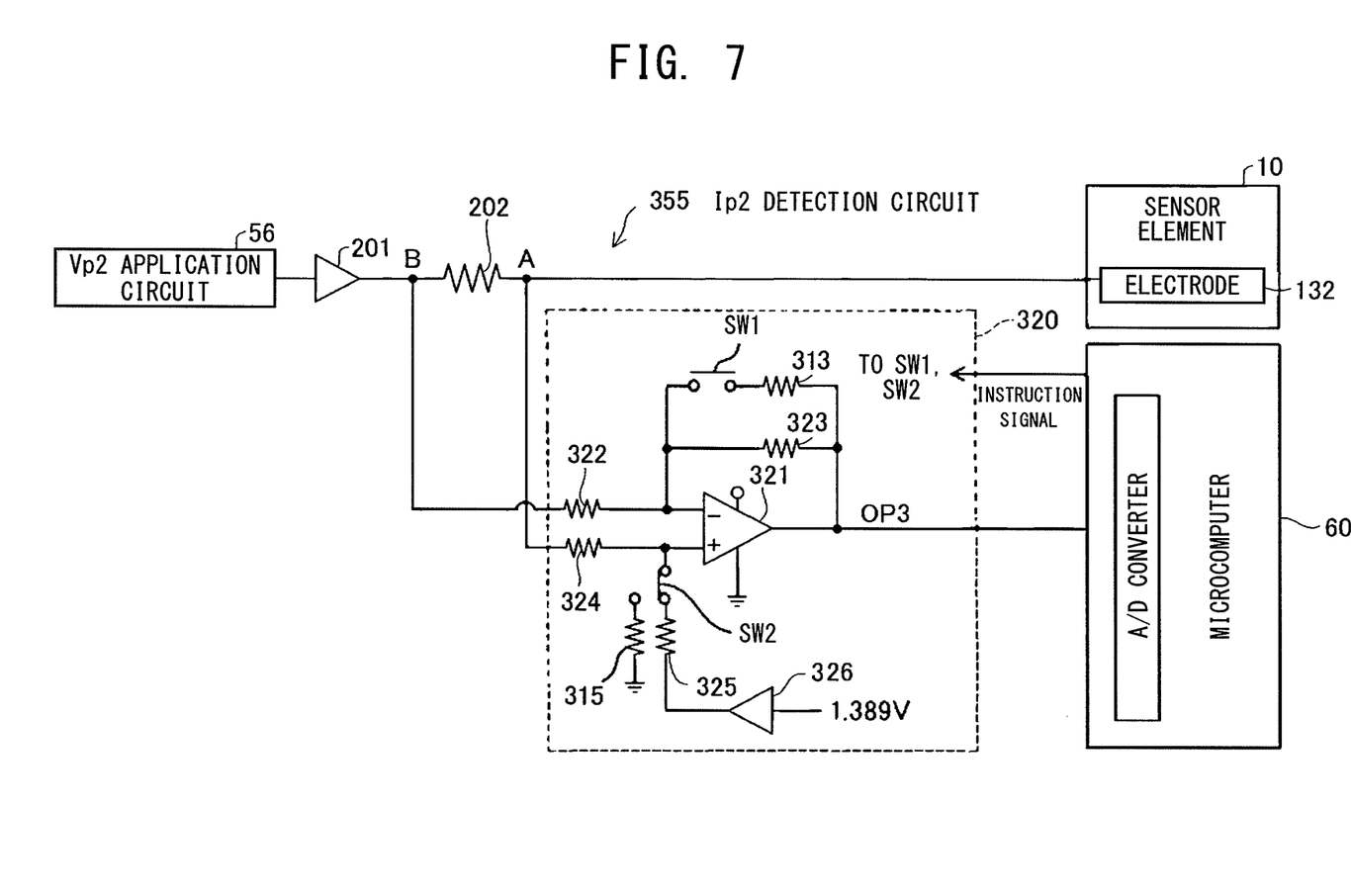
FIG. 7 Diagram showing the circuit configuration of an Ip2 detection circuit 355 in a sensor control device according to a third embodiment of the present invention.

A sensor control device according to a third embodiment of the present invention will now be described. The sensor control device of the third embodiment is identical with the sensor control device 5 of the first embodiment, except for the configuration of the Ip2 detection circuit and the details of the anomaly diagnosis processing. FIG. 7 is a diagram showing the circuit configuration of an Ip2 detection circuit 355 of the third embodiment. The sensor control device of the third embodiment differs from the sensor control device 5 of the first embodiment in that the Ip2 detection circuit 355 includes a single differential amplification circuit (third differential amplification circuit) 320, and the third differential amplification circuit 320 is configured such that its amplification factor is switchable. Notably, in FIG. 7, elements (specifically, the sensor element 10, the Vp2 application circuit 56, the buffer 201, the current detection resistor 202, the microcomputer 60, and the A/D converter 65) identical with those shown in FIG. 1 are denoted by the same reference numerals.

In the Ip2 detection circuit 355 of the third embodiment, the third differential amplification circuit 320 is connected to points A and B located at the opposite ends of the current detection resistor 202, and the output OP3 of the third differential amplification circuit 320 is input to the A/D converter 65 of the microcomputer 60. In this third differential amplification circuit 320, the potential at the point A is applied to the noninverting input terminal (+input pin) of the operational amplifier 321 via a resistor 324, and an offset voltage (offset) of 1.389 V or 0 V is also applied to the +input pin via a switch SW2. That is, in the case where the switch SW2 is connected to a resistor 325, 1.389 V is applied to the +input pin of the operational amplifier 321 via a resistor 325 and a buffer 326. Meanwhile, in the case where the switch SW2 is connected to a resistor 315, 0 V is applied to the +input pin of the operational amplifier 321 via the resistor 315.

Also, in the third differential amplification circuit 320, the potential at the point B is applied to the inverting input terminal (−input pin) of the operational amplifier 321 via a resistor 322, and the output of the operational amplifier 321 itself is also applied to the −input pin via a resistor 323. Notably, a circuit including a switch SW1 and a resistor 313 connected in series is connected in parallel to the resistor 323. Therefore, by means of turned the switch SW1 on and off, the resistance of a feedback resistor present between the −input pin of the operational amplifier 221 and the output of the operational amplifier 321 itself can be switched to either of the resistance of the resistor 323 and the combined resistance of the resistors 323 and 313 connected in parallel. Through this switching, the amplification factor (gain) of the third differential amplification circuit 320 can be switched to either of a first amplification factor (10) and a second amplification factor (24).

Notably, the third differential amplification circuit 320 is configured such that the switch SW1 is switched in synchronism with the switch SW2 on the basis of an instruction from the microcomputer 60. Specifically, when the switch SW1 is turned on and the switch SW2 is connected to the resistor 315, the amplification factor becomes 10, and the offset becomes 0 V. Meanwhile, when the switch SW2 is turned off and the switch SW2 is connected to the resistor 325, the amplification factor becomes 24, and the offset becomes 1.389 V. Since the output OP3 of the third differential amplification circuit 320 at the time when the amplification factor is switched to 10 falls within the range of operation voltage (e.g., 0 to 5 V) of the A/D converter 65 when the $NO_X$ concentration falls within the predetermined wide range, the third differential amplification circuit 320 can output a proper signal within the wide range. Meanwhile, since the output OP3 of the third differential amplification circuit 320 at the time when the amplification factor is switched to 24 falls within the range of operation voltage of the A/D converter 65 when the $NO_X$ concentration falls within the predetermined narrow range, the third differential amplification circuit 320 can output a proper signal within the narrow range.

Next, there will be described anomaly diagnosis for the sensor control device performed by the microcomputer 60 in the sensor control device of the third embodiment including the Ip2 detection circuit 355.

Figure 8:
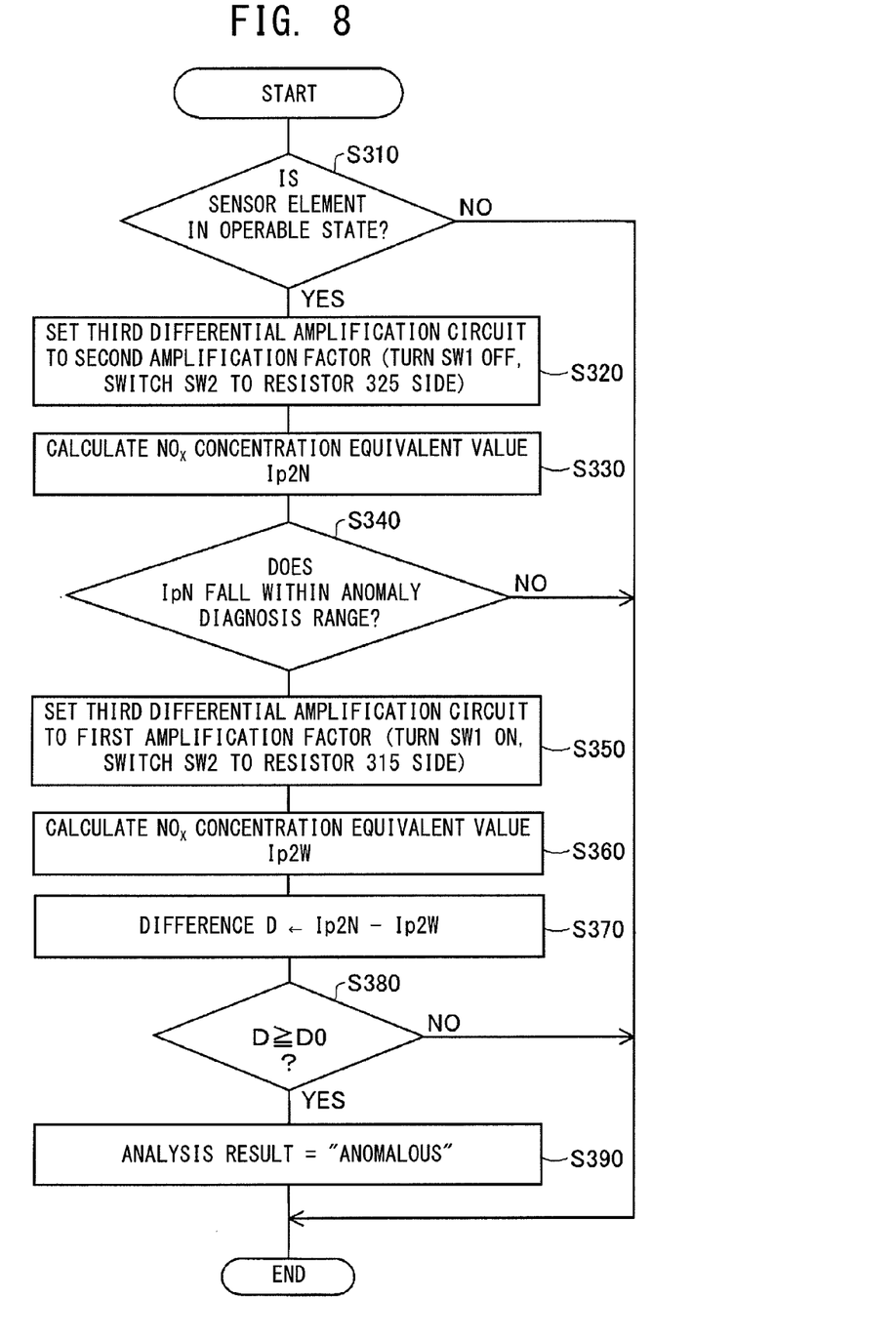
FIG. 8 Flowchart showing anomaly diagnosis processing executed in the sensor control device according to the third embodiment of the present invention.

FIG. 8 is a flowchart showing anomaly diagnosis processing executed by the CPU of the microcomputer 60. In the sensor control device of the third embodiment, after the sensor control device is started, this anomaly diagnosis processing is periodically executed by means of interruption processing. In the anomaly diagnosis processing, the CPU first determines whether or not the sensor element 10 is in an operable state (step S310). Since this determination processing is identical with the processing of step S110 in the first embodiment, its description will be omitted.

When the CPU determines in step S310 that the sensor element 10 is not in the operable state, the CPU ends the anomaly diagnosis processing. Meanwhile, when the CPU determines in step S310 that the sensor element 10 is in the operable state, the CPU issues instructions for turning the switch SW1 off so as to set the amplification factor of the third differential amplification circuit 320 to 24 (the second amplification factor), and connecting the switch SW2 to the resistor 325 (step S320). With this processing, the amplification factor of the third differential amplification circuit 320 is set to 24, and the offset thereof is set to 1.389 V. Subsequently, the CPU proceeds to step S330 so as to take in the A/D converted value of the output OP3 of the third differential amplification circuit 320 and obtain a second $NO_X$ concentration ($NO_X$ concentration equivalent value) Ip2N by multiplying the A/D converted value of the output OP3 by a predetermined value.

After execution of step S330, the CPU determines whether or not the second $NO_X$ concentration Ip2N falls within the anomaly diagnosis range ZN (see FIG. 4) (step S340). When the CPU determines in step S340 that the second $NO_X$ concentration Ip2N does not fall within the anomaly diagnosis range ZN, the CPU ends the anomaly diagnosis processing. Meanwhile, when the CPU determines in step S340 that the second $NO_X$ concentration Ip2N falls within the anomaly diagnosis range ZN, the CPU proceeds to step S350, and issues instructions for turning the switch SW1 on so as to set the amplification factor of the third differential amplification circuit 320 to 10 (the first amplification factor), and connecting the switch SW2 to the resistor 315. With this processing, the amplification factor of the third differential amplification circuit 320 is set to 10, and the offset thereof is set to 0 V. Subsequently, the CPU proceeds to step S360, in which the CPU takes in the A/D converted value of the output OP3 of the third differential amplification circuit 320 and obtains a first $NO_X$ concentration ($NO_X$ concentration equivalent value) Ip2W by multiplying the A/D converted value of the output OP3 by a predetermined value.

After execution of step S360, the CPU calculates the difference D by subtracting the first $NO_X$ concentration Ip2W from the second $NO_X$ concentration Ip2N (step S370). Subsequently, in step S370, the CPU determines whether or not the calculated difference D is equal to or greater than a predetermined value D0 (e.g., 200 ppm) set for anomaly determination. In the case where the CPU determines in step S370 that the difference D is equal to or greater than the predetermined value D0, the CPU determines that the result of the analysis is "anomalous" (step S390). Notably, this diagnosis result is reported to the outside, for example, by sending the result to the ECU. Meanwhile, in the case where the CPU determines in step S390 that the difference D is less than the predetermined value D0, the CPU ends the anomaly diagnosis processing without executing step S390.

The sensor control device of the third embodiment having the above-described configuration performs the anomaly diagnosis on the basis of the difference between the first $NO_X$ concentration Ip2W and the second $NO_X$ concentration Ip2N which are obtained by switching the amplification factor of the third differential amplification circuit 320 between the different values. Therefore, the sensor control device of the third embodiment can accurately diagnose or detect a failure in which the input signal from the differential amplification circuit assumes an anomalous value within in the intermediate range.

C. Modifications

First Modification:

In the above-described first to third embodiments, anomaly diagnosis is performed on the basis of the difference D between the first $NO_X$ concentration Ip2W and the second $NO_X$ concentration Ip2N. However, the embodiments may be configured to perform anomaly diagnosis on the basis of the ratio between the first $NO_X$ concentration Ip2W and the second $NO_X$ concentration Ip2N. For example, the embodiments may be configured to obtain the ratio and determine that an anomaly occurs when the ratio is equal to or greater than a predetermined value for anomaly determination. Moreover, the present invention is not limited to the configuration in which anomaly diagnosis is performed on the basis of the difference or the ratio, and any other configuration may be employed, so long as the first $NO_X$ concentration Ip2W and the second $NO_X$ concentration Ip2N are compared with each other.

Second Modification:

In the first and second embodiments, when anomaly determination is performed, a determination is made as to whether or not at least one of the first and second $NO_X$ concentrations Ip2W and Ip2N falls within the anomaly diagnosis range ZN. However, the first and second embodiments may be configured to determine whether or not the first $NO_X$ concentrations Ip2W falls within the anomaly diagnosis range ZN (such determination is not made for the second $NO_X$ concentration Ip2N). Alternately, the first and second embodiments may be configured to determine whether or not the second $NO_X$ concentrations Ip2N falls within the anomaly diagnosis range ZN (such determination is not made for the first $NO_X$ concentration Ip2W). In the above-described first and second embodiments, anomaly diagnosis can be performed for both the signal system including the first differential amplification circuit 210 and the signal system including the second differential amplification circuit 220. In contrast, in the second modification, anomaly diagnosis can be performed only for the signal system including the differential amplification circuit for which it is determined that the corresponding $NO_X$ concentration Ip2 falls within the anomaly diagnosis range ZN.

Third Modification:

In the above-described first to third embodiments, the wide range serving as the first detection range (0 to 700 ppm) and the narrow range serving as the second detection range (−100 to 200 ppm) partially overlap each other. However, the narrow range may be set to be 0 to 200 ppm such that the wide range includes the narrow range. Furthermore, in the first and second embodiments, the first differential amplification circuit 210 has a gain of 10 and an offset of 0 V, and the second differential amplification circuit 220 has a gain of 24 and an offset of 1.389 V; and, in the third embodiment, the third differential amplification circuit 320 is configured to be switchable between the state in which the gain is 10 and the offset is 0 V and the state in which the gain is 24 and the offset is 1.389 V. However, the gain and offset may be set arbitrarily, so long as the first detection range and the second detection range partially overlap each other.

Fourth Modification:

In the first embodiment, 16 fields FD1 to FD16 are provided in the difference accumulation buffer BF, and 16 values of the difference obtained through continuous sampling up to the present are integrated. However, the first embodiment may be configured to integrate sampled values of the difference in an number other than 16. Notably, in this case, the threshold Di0 for the difference integrated value Dint is a value which depends on the number and which differs from that used in the first embodiment.

Fifth Modification:

The configuration of the gas sensor 1 controlled by the sensor control device 5 and the configuration of the sensor element 10 provided in the gas sensor 1 can be changed freely. For example, the gas sensor 1 (sensor element 10) of the present mode has the Vs cell 120 under the first measurement chamber 150 as shown in FIG. 1. However, the present invention may be applied to a sensor control device for controlling a gas sensor which does not include the Vs cell 120.

Sixth Modification:

In the above-described first to third embodiments, the sensor control device is configured to be used with the gas sensor 1 which can detect the concentration of $NO_X$. However, the sensor control device may configured to be used with a gas concentration sensor which can detect, as a chemical quantity, the concentration of oxygen, the concentration of HC, or the concentration of CO. Furthermore, the sensor control device may be applied to gas concentration detection apparatuses other than those for automobiles. The gas to be detected is not limited to exhaust gas and may be intake gas. Furthermore, the sensor is not limited to the gas concentration sensor, and may be a sensor for detecting any other chemical quantity such as the concentration of a specific component contained in a liquid to be measured. Moreover, the quantity to be detected is not limited to chemical quantities, and the sensor control device may be configured to be used with a sensor which detects a physical quantity, such as the temperature or pressure of a gas to be measured.

In the above-described embodiments and modifications, a portion of the configuration realized by hardware may be replaced with software, and a portion of the configuration realized by software may be replaced with hardware.

Notably, among the constituent elements in the above-described embodiments and modifications, elements other than those described in the independent claims are additional elements, and may be omitted. Also, the present invention is not limited to the above-described embodiments and modifications, and may be practiced in various forms without departing from the scope of the present invention.

DESCRIPTION OF REFERENCE NUMERALS

1: gas sensor
5: sensor control device
10: sensor element
51: reference voltage comparison circuit
52: Ip1 drive
53: Vs detection circuit
54: Icp supply circuit
55, 355: Ip2 detection circuit
56: Vp2 application circuit
57: heater drive circuit
58: electric circuit section
60: microcomputer
61: CPU
62: RAM
63: ROM
64: signal input/output section
65: A/D converter
90: ECU
111, 131: solid electrolyte member
112, 113, 132, 133: electrode
130: Ip2 cell
150: first measurement chamber
151: first diffusion resistance portion
152: second diffusion resistance portion
160: second measurement chamber
201: buffer
202: current detection resistor
210: first differential amplification circuit
211: operational amplifier
220: second differential amplification circuit
221: operational amplifier
226: buffer
320: third differential amplification circuit
321: operational amplifier
Ip2W: first $NO_X$ concentration
Ip2N: second $NO_X$ concentration
D: difference
Dint: difference integrated value
BF: difference accumulation buffer
ZN: anomaly diagnosis range
SW1, SW2: switch

The invention claimed is:

1. A sensor control device comprising:

a sensor section which outputs an electric signal value corresponding to a physical or chemical characteristic of a measurement subject;

a first amplification section which receives the electric signal value output from the sensor section and amplifies the electric signal value at a first amplification factor for a first detection range of the characteristic;

a second amplification section which receives the electric signal value output from the sensor section and amplifies the electric signal value at a second amplification factor for a second detection range of the characteristic, at least a portion of the second detection range overlapping with the first detection range; and a control section which obtains a value representing the characteristic on the basis of an output from the first amplification section and an output from the second amplification section, and which outputs the value as a sensor detection value, the sensor control device being characterized by further comprising:

an equivalent value acquisition section for acquiring a first characteristic equivalent value based on the output from the first amplification section and a second characteristic equivalent value based on the output from the second amplification section;

an equivalent value determination section for determining whether or not at least one of the first and second characteristic equivalent values falls within an anomaly diagnosis range, which is a predetermined range contained in an overlap portion between the first detection range and the second detection range; and an anomaly diagnosis section configured such that, when the equivalent value determination section determines that at least one of the first and second characteristic equivalent values falls within an anomaly diagnosis range, the anomaly diagnosis section determines whether or not an anomaly has occurred in at least one of a signal system containing the first amplification section and a signal system containing the second amplification section, through comparison between the first characteristic equivalent value and the second characteristic equivalent value.

2. A sensor control device according to claim 1, wherein the anomaly diagnosis section comprises:
   a difference calculation section for calculating the difference between the first characteristic equivalent value and the second characteristic equivalent value; and
   an anomaly determination section for determining the occurrence of an anomaly on the basis of the calculated difference.

3. A sensor control device according to claim 2, wherein the difference calculation section includes an integrated value calculation section for obtaining an integrated value of the difference over a predetermined period; and
   the anomaly determination section determines that an anomaly has occurred when the integrated value becomes equal to or greater than a predetermined value.

4. A sensor control device according to claim 3, wherein the equivalent value acquisition section is configured to acquire the first characteristic equivalent value and the second characteristic equivalent value at predetermined intervals shorter than the predetermined period;
   the difference calculation section is configured to obtain, at the predetermined intervals, an integrated value of the difference by integrating a plurality of values of the difference between the first characteristic equivalent value and the second characteristic equivalent value acquired by the equivalent value acquisition section, the plurality of values being obtained through continuous sampling up to the present; and
   the anomaly determination section determines, at the predetermined intervals, that an anomaly has occurred when the integrated value calculated by the difference calculation section becomes equal to or greater than a predetermined value.

5. A sensor control device according to claim 1, wherein the second detection range is narrower than the first detection range; and the second amplification factor is greater than the first amplification factor.

6. A sensor control device according to claim 1, comprising a plurality of amplification circuits which receive the electric signal value output from the sensor section, wherein one of the amplification circuits constitutes the first amplification section which amplifies the electric signal value at the first amplification factor, and another of the amplification circuits constitutes the second amplification section which amplifies the electric signal value at the second amplification factor.

7. A sensor control device according to claim 1, comprising an amplification circuit which receives the electric signal value output from the sensor section, wherein the amplification factor of the amplification circuit can be switched between the first amplification factor and the second amplification factor, the first amplification section is constituted when the amplification factor of the amplification circuit is set to the first amplification factor, and the second amplification section is constituted when the amplification factor of the amplification circuit is set to the second amplification factor.

8. A sensor control device according to claim 1, wherein the characteristic is the concentration of a specific gas contained in the measurement subject.

9. A sensor control method which uses a sensor section which outputs an electric signal value corresponding to a physical or chemical characteristic of a measurement subject, a first amplification section which receives the electric signal value output from the sensor section and amplifies the electric signal value at a first amplification factor for a first detection range of the characteristic, and a second amplification section which receives the electric signal value output from the sensor section and amplifies the electric signal value at a second amplification factor for a second detection range of the characteristic, at least a portion of the second detection range overlapping with the first detection range, the method obtaining a value representing the characteristic on the basis of an output from the first amplification section and an output from the second amplification section, and outputting the value as a sensor detection value,
   the sensor control method being characterized by comprising:
   an equivalent value acquisition step of acquiring a first characteristic equivalent value based on the output from the first amplification section and a second characteristic equivalent value based on the output from the second amplification section;
   a determination step of determining whether or not at least one of the first and second characteristic equivalent values falls within an anomaly diagnosis range, which is a predetermined range contained in an overlap portion between the first detection range and the second detection range; and
   an anomaly diagnosis step of determining, through comparison between the first characteristic equivalent value and the second characteristic equivalent value, whether or not an anomaly has occurred in at least one of a signal system containing the first amplification section and a signal system containing the second amplification section, when it is determined in the determination step that at least one of the first and second characteristic equivalent values falls within an anomaly diagnosis range.

* * * * *